United States Patent [19]

Guigan

[11] Patent Number: 4,788,154
[45] Date of Patent: Nov. 29, 1988

[54] METHOD AND APPARATUS FOR OBTAINING AND DELIVERING A PREDETERMINED QUANTITY OF PLASMA FROM A BLOOD SAMPLE FOR ANALYSIS PURPOSES

[76] Inventor: Jean Guigan, 9 rue Jean Mermoz, 75008 Paris, France

[21] Appl. No.: 944,406

[22] Filed: Dec. 22, 1986

[30] Foreign Application Priority Data

Dec. 20, 1985 [FR] France ............................... 85 18954

[51] Int. Cl.⁴ ..................... G01N 1/28; B01D 21/26; B04B 5/02
[52] U.S. Cl. .................................. 436/180; 210/514; 210/518; 210/787; 422/64; 422/72; 422/102; 436/45; 494/16
[58] Field of Search .................... 356/246; 422/61, 72, 422/64, 102; 436/45, 180; 494/16; 210/514, 518, 787

[56] References Cited

U.S. PATENT DOCUMENTS 4,632,908 12/1986 Schultz ............................ 422/72 X

FOREIGN PATENT DOCUMENTS

0062907 10/1982 European Pat. Off. .
0084983 3/1983 European Pat. Off. .
0160282 11/1985 European Pat. Off. .
2524874 10/1983 France .

Primary Examiner—Benoit Castel
Assistant Examiner—Robert J. Hills, Jr.
Attorney, Agent, or Firm—Sughrue, Mion, Zinn, Macpeak & Sons

[57] ABSTRACT

A method and a device for obtaining plasma from a few microliters of blood for analysis purposes. The method makes use a transfer strip (10) and a turntable for performing centrifuging operations.

4 Claims, 13 Drawing Sheets

METHOD AND APPARATUS FOR OBTAINING AND DELIVERING A PREDETERMINED QUANTITY OF PLASMA FROM A BLOOD SAMPLE FOR ANALYSIS PURPOSES

The present invention relates to a method and to an apparatus for delivering a predetermined quantity of serum or plasma from a blood sample for analysis purposes.

BACKGROUND OF THE INVENTION

This method and apparatus are intended, in particular, to complement the analysis methods and apparatuses described in French patent applications Nos. 8416448 filed Oct. 26, 1984, 8419719 filed Dec. 21, 1984, 8504476 filed Mar. 26, 1985, 8504477 filed Mar. 26, 1985, etc.

When examining blood, blood is taken from a patient by means of a tube including an anticoagulant, and is then centrifuged in order to collect red corpuscles at the end of the tube, with analyses being performed on the plasma located above the corpuscles. Modern analysis techniques require only a very small quantity of plasma, and preferred implementations of the invention provide a method and apparatus enabling very small quantities of plasma to be transferred to the above mentioned analysis apparatuses from a very small initial quantity of blood, thus providing a considerable improvement for the patient.

Preferred implementations of the present invention provide a method of delivering a predetermined quantity of plasma from a blood sample having a volume of a few microliters.

A difficult problem arises when transferring such very small samples of liquid because of the capillary nature of the ducts interconnecting the receptacle to the various cells.

The use of centrifugal force which has the apparent effect of increasing the density of the liquid used serves to overcome the problems of capillary retention.

SUMMARY OF THE INVENTION

The present invention provides a method of delivering at least one predetermined quantity of plasma from a blood sample for analysis purposes, the method comprising the use of the following items:

firstly a longitudinal transfer strip made of transparent plastic material and comprising a housing enclosed by a lid, said housing comprising first and second end faces, first and second longitudinal side faces, and being compartmented so as to present:

along said first longitudinal side face and running from said first end face, a receptacle for receiving a blood sample followed by an outlet channel into which a plasma storage cell and a red corpuscle storage cell opens out; and along said second longitudinal side face and starting from said first end face, a measurement cell connected by a capillary tube firstly to a central plasma removal cell having an outlet orifice through the bottom of said housing, and secondly to an overflow channel opening out into said plasma storage cell and then into an overflow tank, the end of the measurement cell opposite to said capillary tube being connected by a capillary duct to overflow cells which also open out into said overflow channel;

and secondly a turntable rotatable about its center and on which said strip may be disposed radially in two positions A and B, the position A corresponding to said first end face being closer to the center of the turntable than said second end face, and the position B being symmetrical to the position A about the middle of said strip;

said method comprising the steps of:

inserting a sample of a few milliliters of blood through an orifice provided in the lid of a strip so that said blood drops into said receptacle;

disposing said strip in said A position on said turntable and rotating said turntable to cause said sample of blood to pass into said plasma storage cell, said corpuscle storage cell, and said overflow tank, the centrifuging causing plasma to appear in said plasma storage cell and red corpuscles to appear in said corpuscle storage cell;

placing said strip in the B position on said turntable, with rotation of said turntable causing said measurement cell to be filled with plasma from said plasma storage cell; and placing said strip in said A position on said turntable, with rotation of said turntable emptying said measurement cell and causing a calibrated quantity of plasma to pass into said removal cell and thence out from said housing via said outlet orifice.

In a varient implementation, said housing further includes a longitudinal channel running along said second longitudinal side face between the outlets from said overflow cells opposite to the outlet communicating with the measurement cell and a plasma storage tank situated level with said second end face, such that after delivering a calibrated quantity of plasma:

said strip is placed in the B position in order to refill said measurement cell from said storage tank; and said strip is again placed in said A position in order empty said measurement cell into said removal cell.

The present invention also provides a transfer strip for implementing the above method and comprising a housing closed by a lid, both of which are made of transparent plastic material, said housing comprising first and second longitudinal end faces, first and second longitudinal side faces, and being compartmented in such a manner as to present:

along said first longitudinal side face and running from said first end face, a receptacle for receiving a blood sample followed by an outlet channel into which a plasma storage cell and a red corpuscle storage cell opens out; and along said second longitudinal side face and starting from said first end face, a measurement cell connected by a capillary tube firstly to a central plasma removal cell having an outlet orifice through the bottom of said housing, and secondly to an overflow channel opening out into said plasma storage cell and then into an overflow tank, the end of the measurement cell opposite to said capillary tube being connected by a capillary duct to overflow cells which also open out into said overflow channel.

In a variant embodiment, said housing further includes a longitudinal channel running along said second longitudinal side face between the outlets from said overflow cells opposite to the outlet communicating with the measurement cell and a plasma storage tank situated level with said second end face.

BRIEF DESCRIPTION OF THE DRAWINGS

Implementations of the invention are described by way of example with reference to the accompanying drawings, in which.

MORE DETAILED DESCRIPTION

Figure 1A:
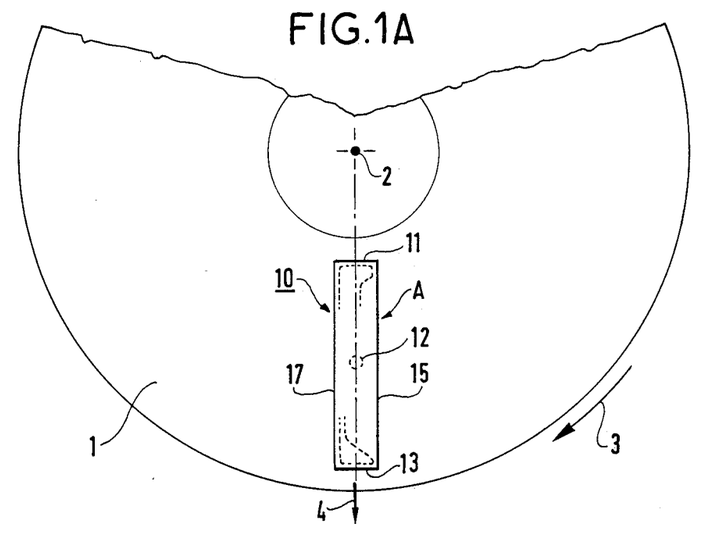
FIGS. 1A and 1B are diagrams showing two positions A and B on a turntable which can be taken up by a transfer strip in accordance with the invention.
Figure 1B:
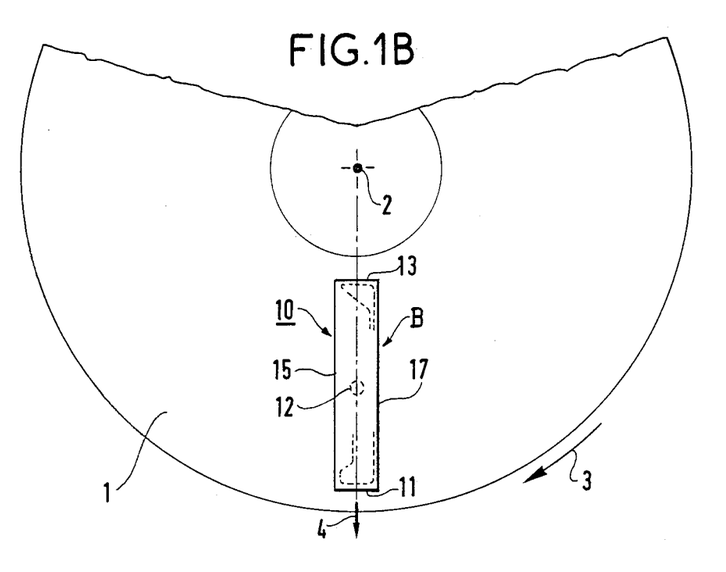

In FIGS. 1A and 1B, reference 1 designates a turntable capable of being rotated about its center 2. Arrow 3 symbolizes rotation of the turntable 1, and arrow 4 indicates the direction in which centrifugal force acts. Transfer strips 10 may be disposed radially on the turntable which is provided with suitable means for pivoting each strip 10 from a first radial position A to a second radial position B which is symmetrically disposed relative to the position A about the center 12 of the strip. References 11 and 13 designate the end faces of the strip and references 15 and 17 designate its longitudinally-extending side faces. By way of example, a strip 10 may be about five centimeters long, about one centimeter wide, and six strips 10 may be placed on a turntable 1 having an overall diameter of about twenty centimeters.

Figure 2:
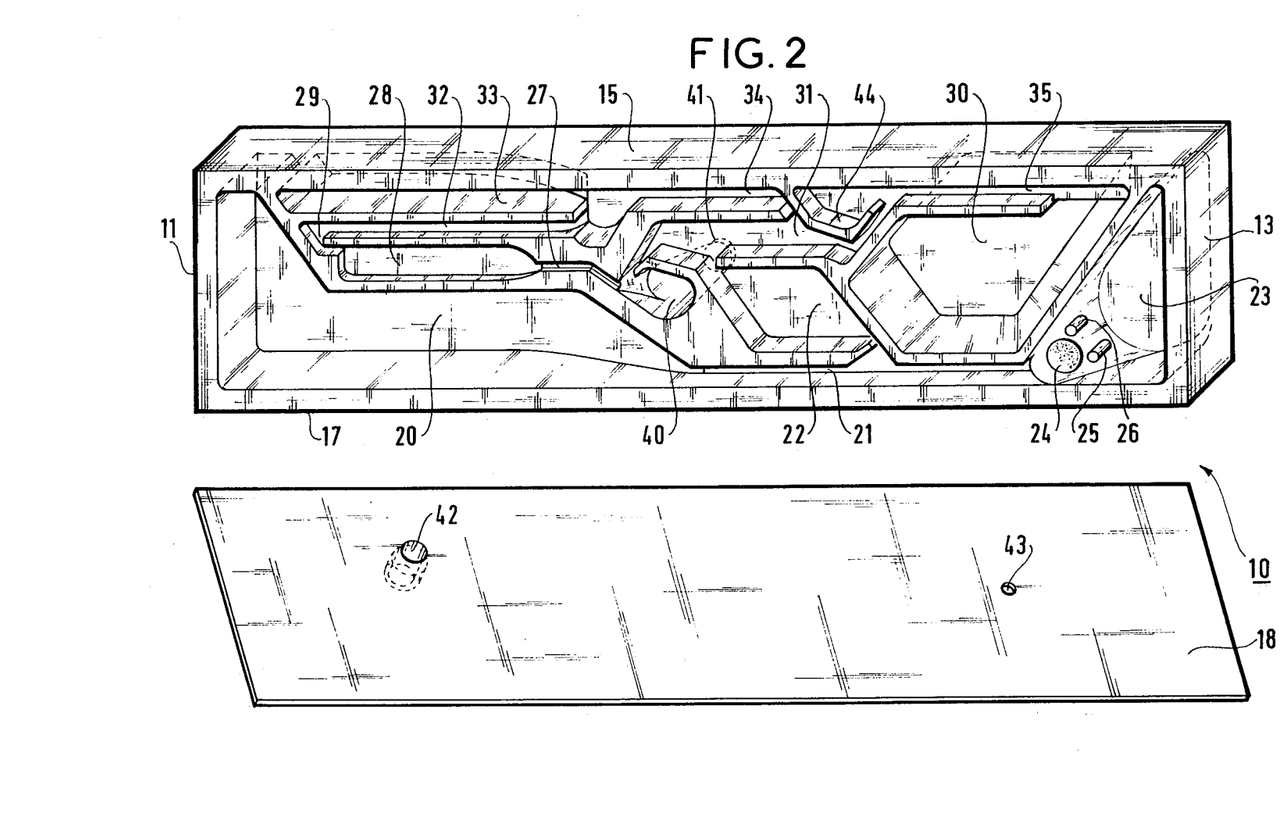
FIG. 2 is an exploded perspective view of a transfer strip usable in implementing the method in accordance with the invention.

A transfer strip 10 as shown in perspective in FIG. 2 comprises a housing closed by a lid 18. The assembly is made of transparent plastic material. The housing contains a plurality of compartments which are described below.

Running from end face 11 towards end face 13 along side face 17, there are:
- a receptacle 20 for receiving a sample of blood;
- an outlet channel 21 running from the receptacle 20;
- a plasma storage cell 22 in communication with the channel 21; and
- a red corpuscle storage cell 23 in communication with the end of the channel 21.

A small ballasted plastic ball 24 is provided in association with two retaining pegs 25 and 26 in the vicinity of the orifice from the channel 21 into the cell 23.

The plasma storage cell 22 is connected firstly via a capillary tube 27 to a measurement cell 28 of calibrated volume, and secondly via an overflow channel 31 to an overflow tank 30.

The receptacle 20 and the measurement cell 28 are situated to one end of the plasma storage cell 22, while the overflow tank 30 and the red corpuscle storage cell 23 are situated to the opposite end thereof.

The measurement cell 28 is connected firstly via a capillary duct 29 to overflow cells 32 and 33, and secondly via a capillary tube to a central plasma-removal cell 40 which is open to the outside via an outlet orifice 41 situated in the bottom of the strip 10.

References 34 and 35 designate respective overflow channels; a baffle 44 is provided between the channels 34 and 35.

The lid 18 has vent 43 and an orifice 42 via which a sample of blood is inserted into the receptacle 20. The overflow cells 32 and 33, the overflow channels 34 and 35, and the overflow tank 30 are disposed along the longitudinal side face 15 of the strip 10 in that order when going from end face 11 to end face 13.

FIGS. 3 to 6 show the strip 10 in position A (FIG. 1A) during various centrifuging stages.

Figure 3:
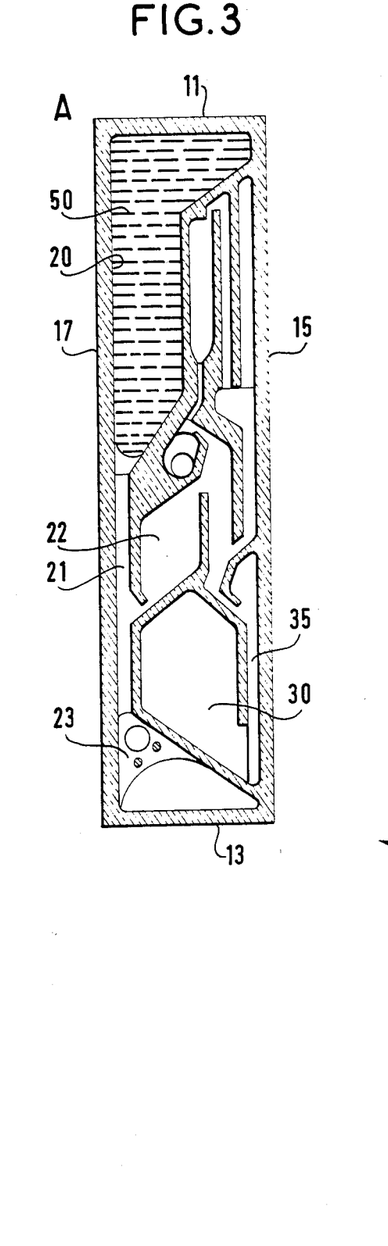
FIGS. 3 to 10 are sections through the FIG. 2 transfer strip as seen from above and showing its contents during different stages of plasma transfer.

In FIG. 3, the strip 10 is in the rest state and the blood sample 50 (a few micrometers) is located in the receptacle 20.

Figure 4:
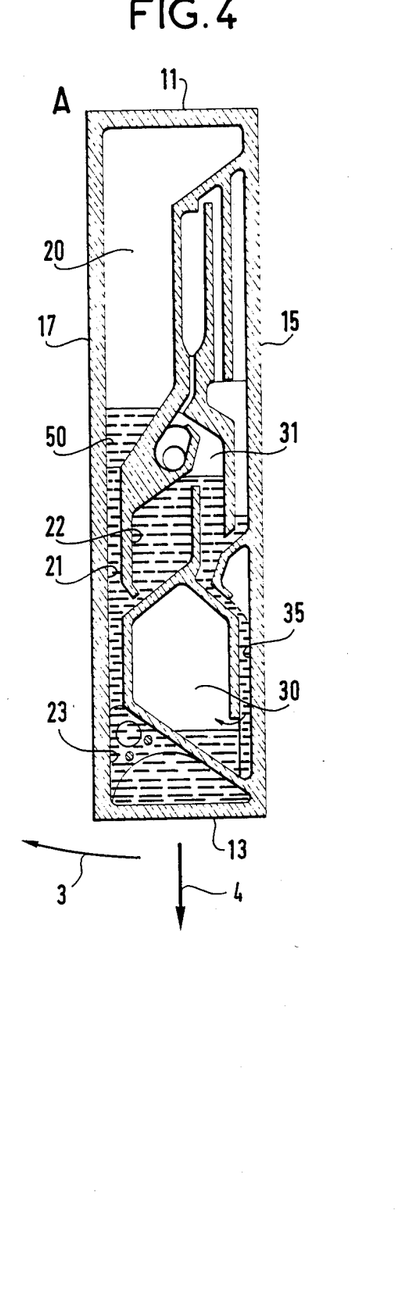
Figure 5:
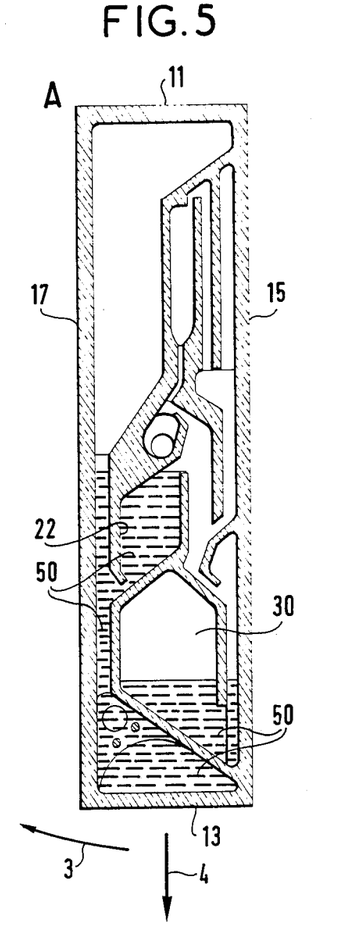

In FIG. 4, centrifuging is taking place and as a result the blood passes under the effect of centrifugal force 4 successively from the receptacle 20 into the channel 21 and then fills the cell 23, thereafter it completely fills the plasma storage cell 22, and the overflow channels 31 and 35, and partially fills the overflow tank 30. This situation is shown in FIG. 5.

Figure 6:
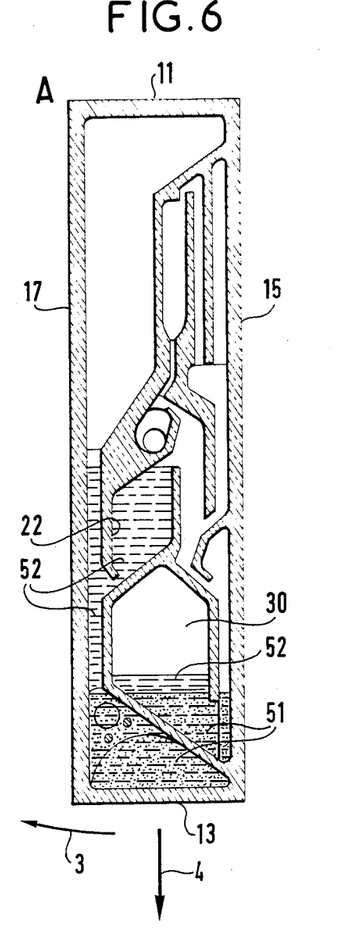

Then, as centrifuging continues, the blood is observed to settle with the red corpuscles 51 and the plasma 52 separating (see FIG. 6).

Figure 7:
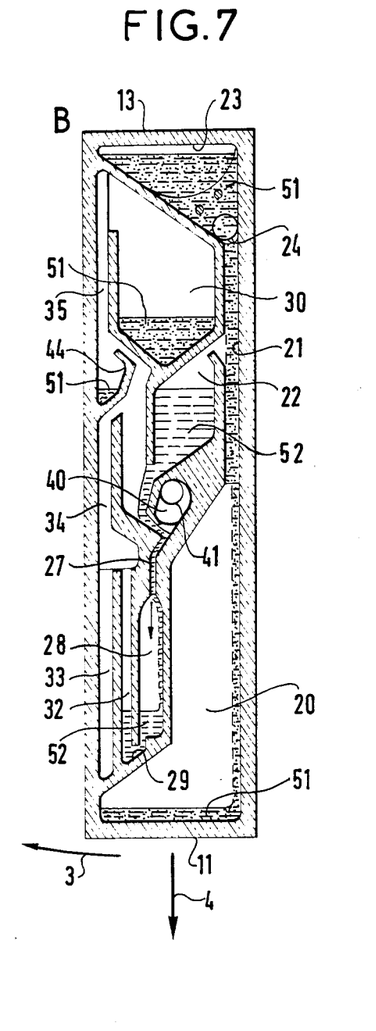
Figure 8:
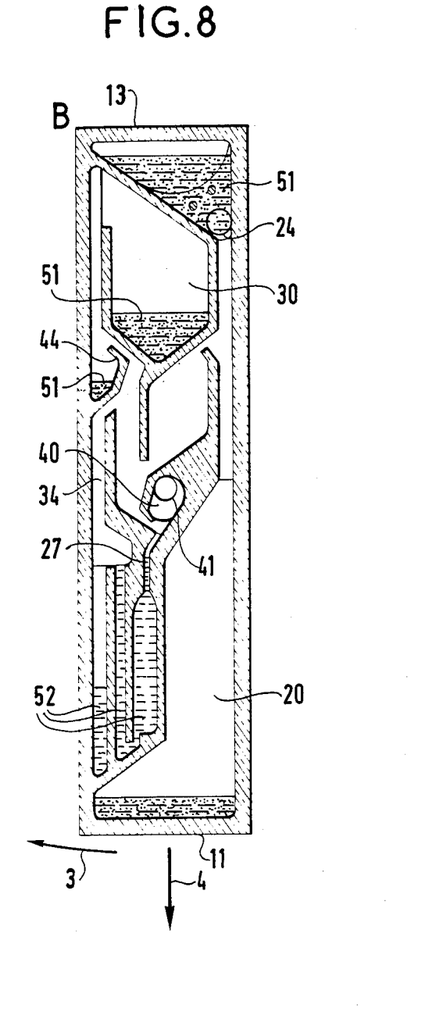

Once separation has occurred, the strip is put into position B (see FIG. 1B). As can be seen in FIGS. 7 and 8, centrifugal force 4 than has the effect of emptying the plasma from the storage cell 22 and filling the capillary tube 27, the measurement cell 28, and then the overflow cells 32 and 33.

The ball 24 closes the orifice providing communication between the red corpuscle storage cell 23 and the channel 21, even though it still allows a small and an unimportant quantity of corpuscles 51 to pass through and accumulate against the end face 11 of the receptacle 20. The baffle 44 provided on the path of the overflow channel 35 serves to trap any red corpuscles 51 which may leave the overflow chamber 30 and be entrained towards the cells 30 and 33 containing plasma (see FIG. 8).

Figure 9:
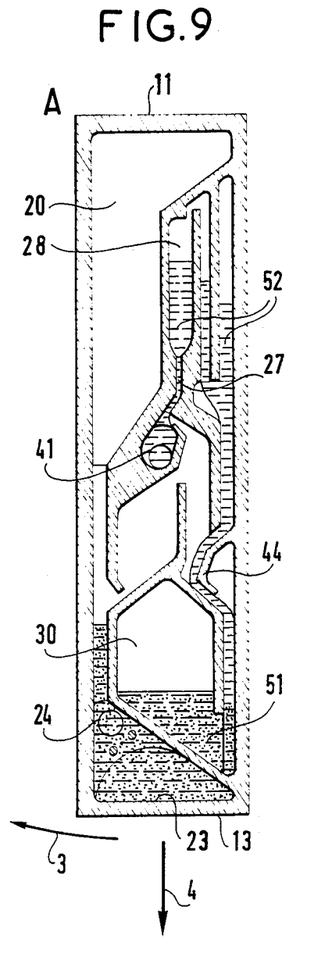
Figure 10:
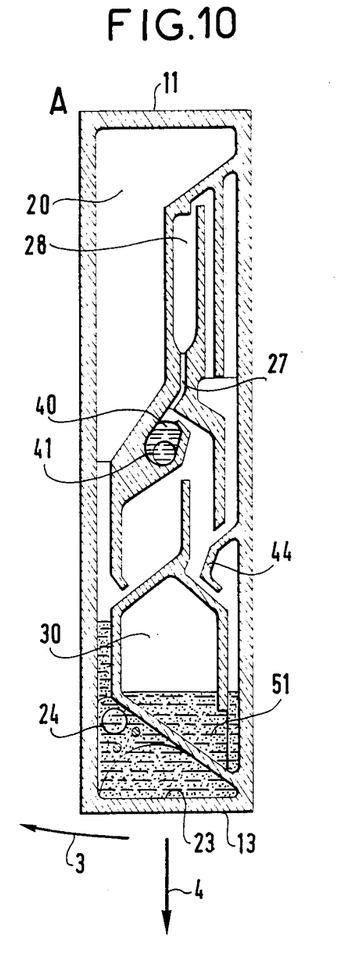

Once this stage is over, the strip is returned to position A (See FIG. 1A). The last stage of the method is now begun (see FIGS. 9 and 10), i.e., the stage in which a calibrated volume of the plasma situated in the measurement cell 28 passes into the plasma removal cell 40 and then leaves it via the orifice 41. The red corpuscles 51 are now held in the cell 23 against a wall of the overflow cell 30.

The calibrated quantity of plasma removed by centrifuging may then be used in a prior art analysis device, for example in one of the devices mentioned above.

Figure 11:
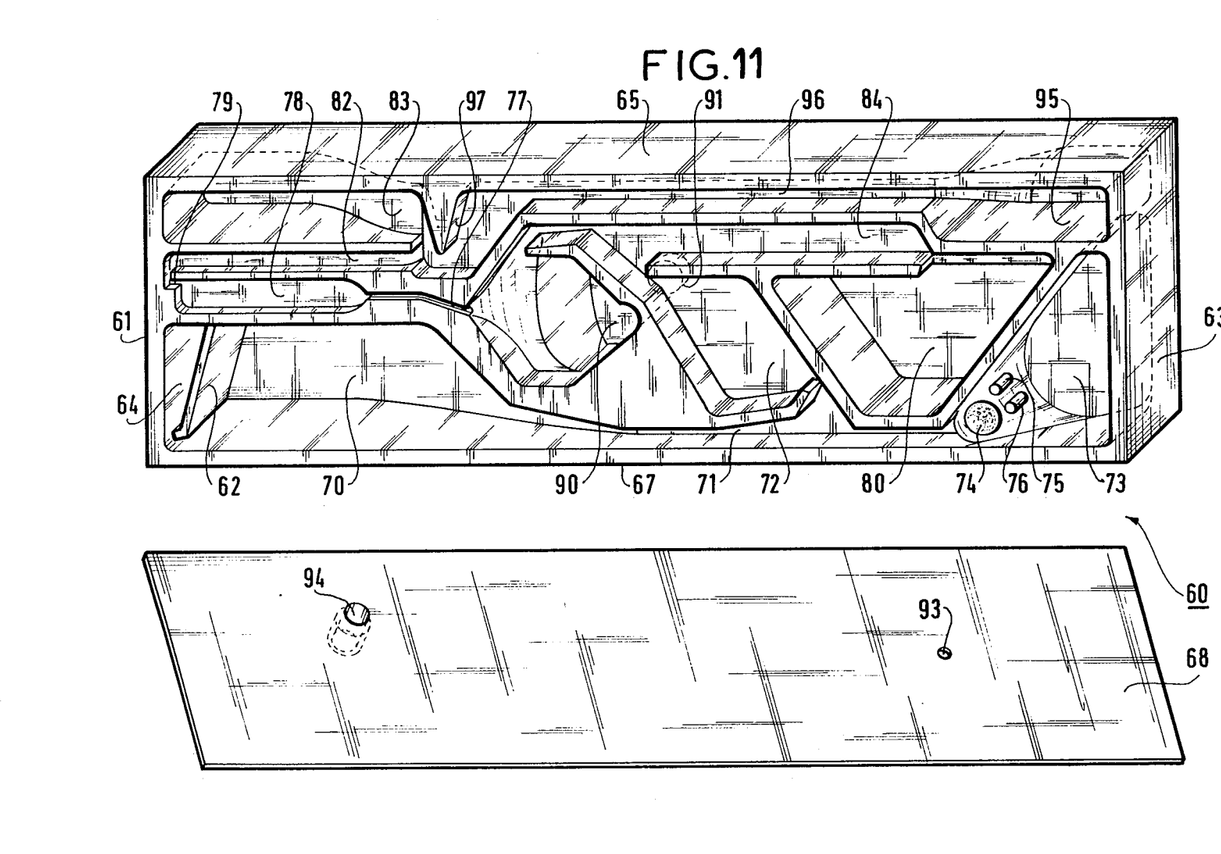
FIG. 11 is an exploded perspective view of another example of a transfer strip for performing the method in accordance with the invention.

FIG. 11 is an exploded perspective view of a variant transfer strip 60 for delivering two calibrated quantities of plasma in succession.

This strip comprises a housing having a lid 68 with a vent 93 and a orifice 94 for inserting a sample of blood.

The end faces of the strip are referenced 61 and 63 and its longitudinal side faces are referenced 65 and 67.

When defining the positions A and B on the turntable, faces 61 and 63 of the strip 60 are respectively equivalent to the faces 11 and 13 of the strip 10.

Along its side face 67, the housing contains a blood receptacle 70, and outlet channel 71 into which a plasma storage cell 72 opens out, and then a red corpuscle storage cell 73.

The receptacle 70 has an additional transverse wall 62 which partially partitions the receptacle and which defines an end compartment 64 therein.

A small ball of ballasted plastic material 74 is associated with two retaining pegs 75 and 76 in the vicinity of the orifice of the channel 71 into the cell 73.

The plasma storage cell 72 is connected firstly via a capillary tube 77 to a measurement cell 78 of calibrated volume, and secondly via an overflow channel 84 to an overflow tank 80.

The measurement cell 78 and the receptacle 70 are situated to one end of the plasma storage cell 72, while the overflow tank 80 and the corpuscle storage cell 73 are situated to the opposite end thereof.

The measurement cell 78 is connected firstly via a capillary duct 79 to plasma overflow cells 82 and 83, and secondly via a capillary tube 77 to a central plasma-removal cell 90 which opens to the outside via an outlet orifice 91 situated in the bottom of the strip 60.

Along the side face 65, and starting from the end face 61, there are an overflow cell 83, a duct 96, and a plasma storage tank 95 whose function is described below.

A baffle 97 is provided in the duct 96 level with the entrance into the overflow cell 83.

FIGS. 12 to 15 show the strip 60 in position A on the turntable (see FIG. 1A).

Figure 12:
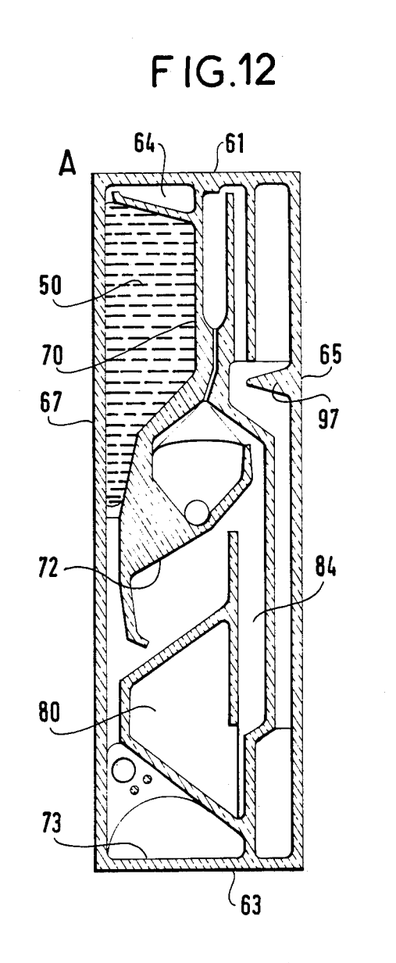
FIGS. 12 to 23 are sections through the FIG. 11 transfer strip as seen from above and showing its contents during different stages of plasma transfer.

In FIG. 12, the strip 60 is at rest and a sample of blood 50 is located in the receptacle 70.

Figure 13:
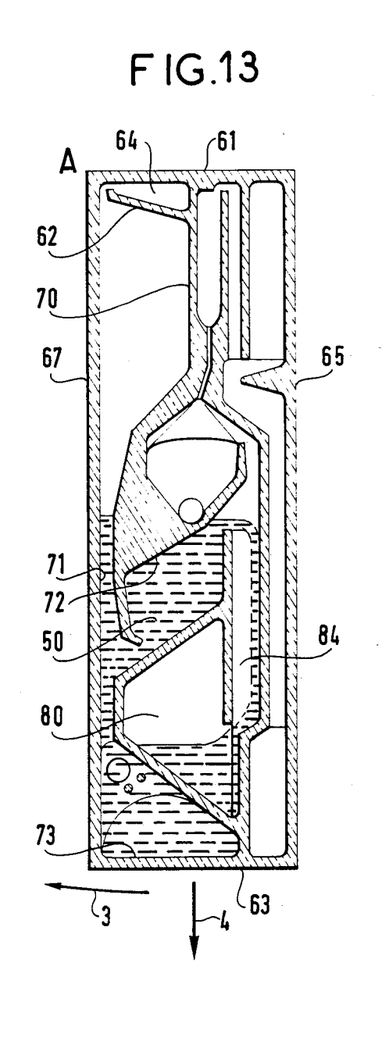
Figure 14:
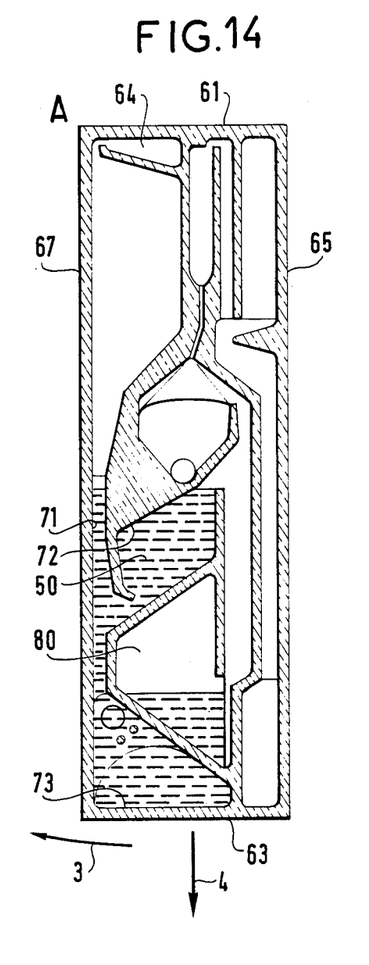
Figure 15:
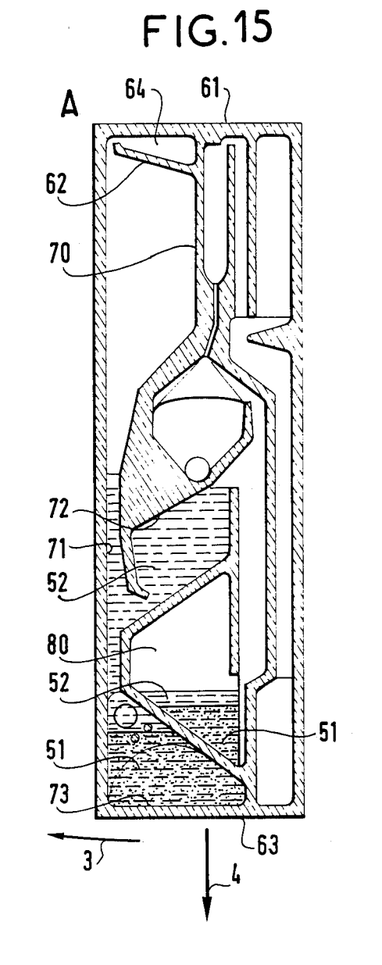

In FIG. 13, the turntable 1 has begun to rotate freely and centrifugal force 4 has the effect of emptying the receptacle 70 via the channel 71 into the plasma storage cell 72, the cell 73, the overflow channel 84, and the overflow tank 80. FIG. 14 shows the strip in this state. As the rotation continues (see FIG. 15) the red corpuscles 51 separate from the plasma and accumulate in the storage cell 73 and in the overflow tank 80. Plasma 52 is to be found in the cell 72, in the channel 71, and in the overflow tank 80.

Figure 16:
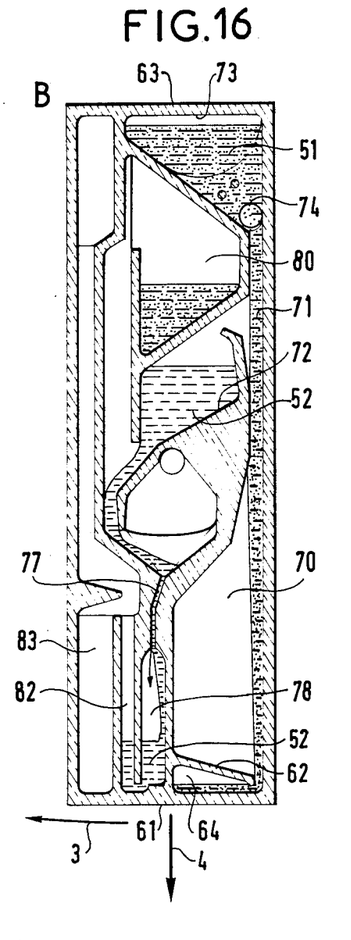

The strip 60 is then put into position B (see FIG. 1B). Centrifugal force 4 now causes the cell 72 to be emptied via the capillary tube 77 (see FIG. 16).

The plasma begins by filling the measurement cell 78, and then the overflow cells 82 and 83. This gives rise to the situation shown in FIG. 17.

Figure 17:
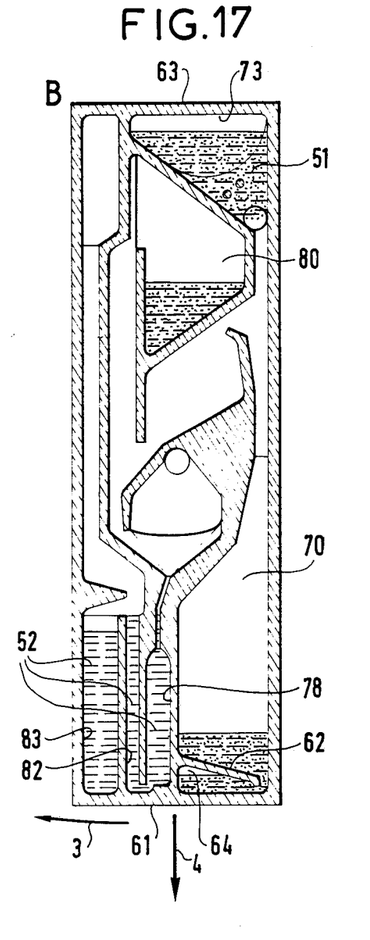

At the same time, a few rod corpuscles present in the cell 73 manage to pass into the receptacle 70 and into the compartment 64, in spite of the channel 71 being closed by the ball 74.

The strip 60 is then returned to position A (see FIG. 1A). As a result centrifugal force 4 has the effect of passing a calibrated quantity of plasma 52 from the calibrated cell 78 into the removal cell 90 via the capillary tube 77 (see Figure 18). This calibrated quantity is removed via the outlet orifice 91 (see FIG. 19). Simultaneously, the excess plasma present in the overflow cells runs via the duct 96 into a plasma storage tank 95. The red corpuscles are stored in the cell 73, the overflow tank 80 and the compartments 64.

Figure 20:
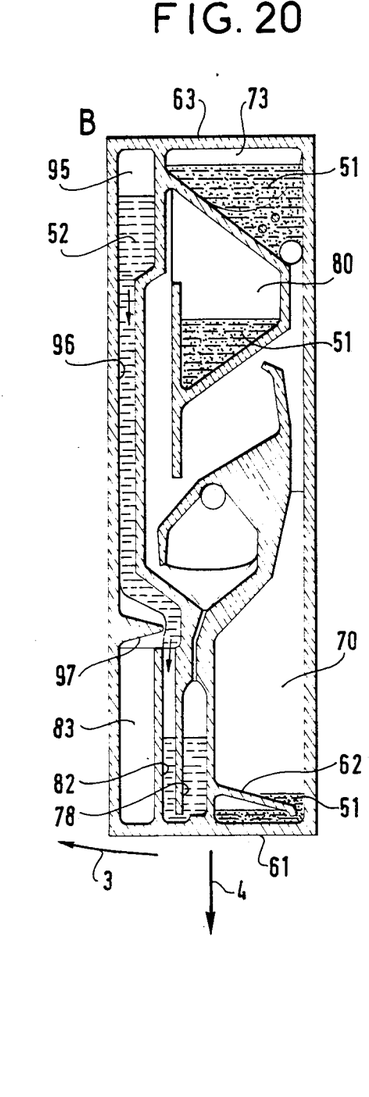

In order to obtain a second calibrated quantity of plasma, the strip 60 is returned to position B (see FIG. 1B). The plasma 52 present in the tank 95 passes along the duct 86 and fills the cell 82 and the measurement cell 78. The baffle 97 prevents the plasma from moving into the overflow cell 83 before it has filled the cells 78 and 82 (see FIG. 20).

Figure 21:
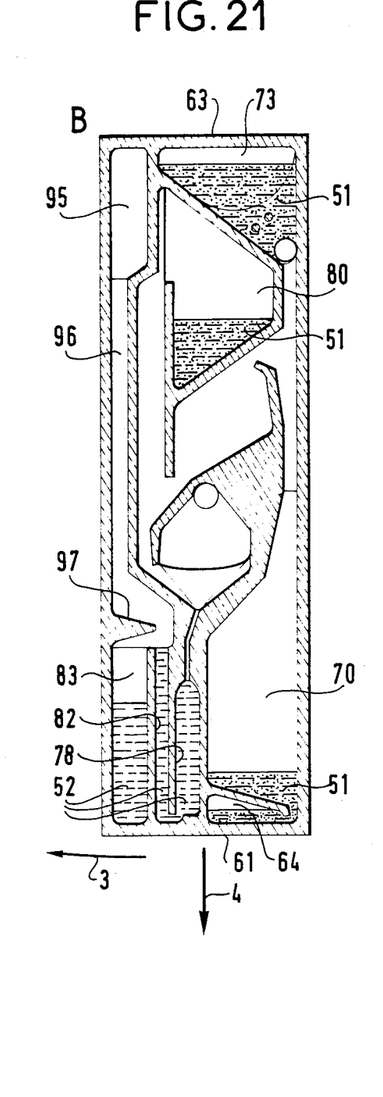

FIG. 21 shows the end of this stage.

Figure 18:
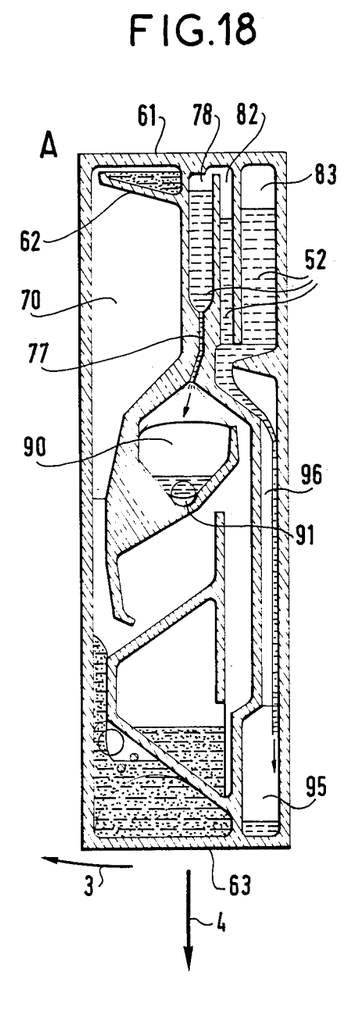
Figure 19:
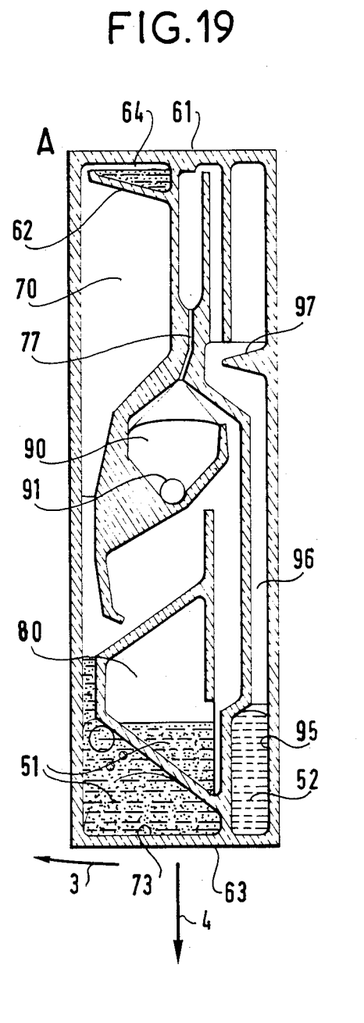
Figure 22:
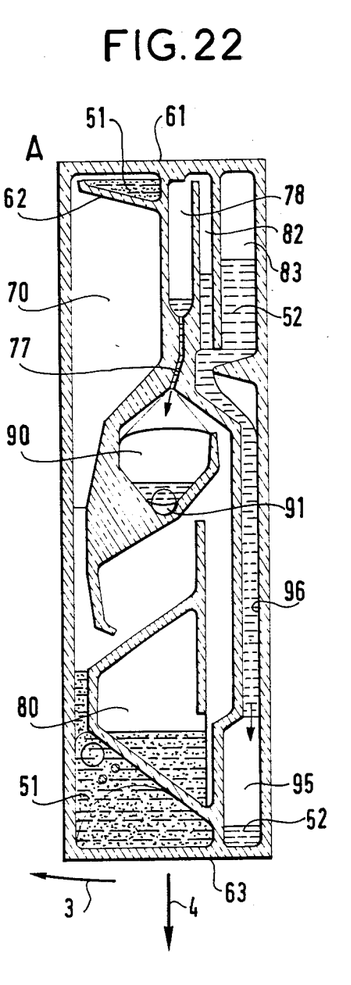
Figure 23:
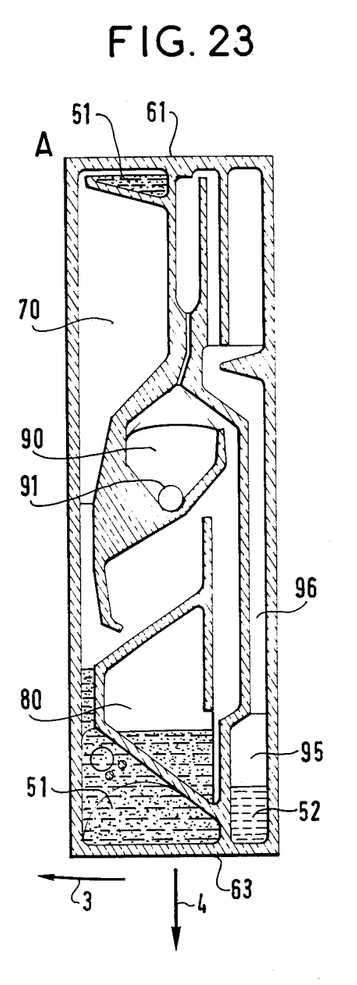

Finally, the strip is returned once more to position A and returns to the situation illustrated in FIGS. 18 and 19 (see FIGS. 22 and 23). A measured quantity of plasma 52 from the measurement cell 78 is removed via the orifice 91 from the cell 90.

If enough plasma remains in the tank 95, the same operation may be repeated once more.

Naturally, without going beyond the scope of the invention, any of the means described may be replaced by equivalent means. A strip in accordance with the invention is easily made by molding techniques.

What is claimed is:

1. A method of delivering at least one predetermined quantity of plasma from a blood sample for analysis purposes, the method making use of the flowing items:

a longitudinal transfer strip made of transparent plastic material and comprising a housing enclosed by a lid, said housing comprising a bottom, first and second opposing end faces, first and second opposing longitudinal side faces, and being compartmented so as to present:

along said first longitudinal side face and running sequentially from said first end face, a receptacle for receiving a blood sample connected to an outlet channel, a plasma storage cell and a red corpuscle storage cell opening into said outlet channel; and parallel to said second longitudinal side face and starting from said first end face, a measurement cell connected by a capillary tube to a central plasma removal cell, having an outlet orifice through the bottom of said housing, and then to an overflow channel which opens into said plasma storage cell and then into an overflow tank, an end of the measurement cell opposite to said capillary tube being connected by a capillary duct to overflow cells;

and a turntable rotatable about its center and on which said transfer strip may be disposed radially in two positions A and B, the position A being one where said first end face is closer to the center of the turntable than said second end face, and the position B being one where the strip is symmetrical to that of position A and where the second end face is closer to the center of the turntable than the first end face;

said method comprising the steps in sequence of:

inserting a sample of a few millimeters of blood through an orifice provided in said lid of said transfer strip so that said blood drops into said receptacle;

disposing said transfer strip in said A position on said turntable and rotating said turntable to cause said sample of blood to pass into said plasma storage cell, said corpuscle storage cell, and said overflow tank, the rotating causing plasma to appear in said plasma storage cell and red corpuscles to appear in said corpuscle storage cell;

placing said transfer strip in the B position on said turntable, and rotating said turntable thereby causing said measurement cell to be filled with plasma from said plasma storage cell; and placing said transfer strip in said A position on said turntable, and further rotating said turntable thereby emptying said measurement cell and causing a calibrated quantity of plasma to pass into said removal cell and thence out from said housing via said outlet orifice.

2. The method according to claim 1, wherein said housing further includes a longitudinal channel running along said second longitudinal side face between outlets of said overflow cells opposite to their connection with the measurement cell via the capillary duct and a plasma storage tank situated adjacent to said second end face, and wherein said method further comprises, after causing the calibrated quantity of plasma to pass into said removal cell and thence out from said housing via said outlet orifice:

placing said transfer strip in the B position and rotating said turntable in order to refill said measurement cell from said storage tank; and again placing said transfer strip in said A position and again rotating said turntable in order to empty said measurement cell into said removal cell.

3. A transfer strip for supplying at least one predetermined quantity of plasma from a blood sample for analysis purposes by disposing said transfer strip radially on a turntable rotatable about its center and periodically rotating said transfer strip by 180° into two positions A and B, the position A corresponding to a position where one end face is closer to the center of the turntable than the other end face and the position B being one where the transfer strip is symmetrical to that at position A with the other end face closer to the center of the turntable and said one end face further therefrom; and rotating said turntable sequentially after changing the transfer strip alternately from position A to position B, said transfer strip comprising:

a housing, a lid closing said housing, both said lid and said housing being made of transparent plastic material, said housing comprising first and second longitudinal end faces, first and second longitudinal side faces and a bottom, and including compartmented means defining:

along said first longitudinal side face and running sequentially from said first end face, a receptacle for receiving a blood sample connected to an outlet channel, a plasma storage cell and a red corpuscle storage cell opening to said outlet channel; and parallel to said second longitudinal side face and starting from said first end face, a measurement cell connected by a capillary tube to a central plasma removal cell, having an outlet orifice extending through said bottom of said housing, and then to an overflow channel which opens into said plasma storage cell and then into an overflow tank, and wherein an end of the measurement cell opposite to said capillary tube is connected by a capillary duct to overflow cells.

4. The transfer strip according to claim 3, wherein said housing further includes a longitudinal channel running along said second longitudinal side face between outlets of said overflow cells opposite to their connection with the measurement cell via the capillary duct and a plasma storage tank situated adjacent to said second end face.

* * * * *